United States Patent [19]

Goodnow et al.

[11] Patent Number: 4,530,832
[45] Date of Patent: Jul. 23, 1985

[54] **METHOD OF VACCINATION FOR PREVENTION OF *BORDETELLA BRONCHISEPTICA* INFECTION**

[75] Inventors: Robert A. Goodnow; Floyd J. Shade; Thomas A. Sloboth, all of Omaha, Nebr.

[73] Assignee: Schering Corporation, Madison, N.J.

[21] Appl. No.: 304,215

[22] Filed: Sep. 21, 1981

Related U.S. Application Data

[63] Continuation of Ser. No. 162,539, Jun. 24, 1980, abandoned, which is a continuation-in-part of Ser. No. 967,478, Dec. 7, 1978, abandoned.

[51] Int. Cl.$^3$ .............................................. A61K 39/10
[52] U.S. Cl. ...................................... 424/92; 206/510
[58] Field of Search ........................... 424/92; 206/510

[56] References Cited

U.S. PATENT DOCUMENTS

| | | | |
|---|---|---|---|
| 3,384,544 | 5/1968 | Walton et al. | 424/92 |
| 3,567,585 | 3/1971 | Bloch et al. | 195/96 |
| 3,607,858 | 9/1971 | Querry et al. | 260/112 B |
| 4,225,583 | 9/1980 | Switzer et al. | 424/92 |

FOREIGN PATENT DOCUMENTS

| | | | |
|---|---|---|---|
| 277937 | 11/1965 | Australia | 424/92 |
| 2313078 | 12/1976 | France | |
| 273349 | 7/1927 | United Kingdom | 424/92 |
| 1543783 | 4/1979 | United Kingdom | |

*Primary Examiner*—Shep K. Rose
*Attorney, Agent, or Firm*—Serle I. Mosoff; Stephen I. Miller

[57] ABSTRACT

Viable cells of an avirulent self-clearing strain of *B. bronchiseptica* are administered as an intra-respiratory vaccine. An aqueous suspension of the cells is applied to the respiratory mucosa immediately after incorporating a non-inhibitory amount of a wetting agent promoting the mucosal implantation of the cells. Effective immunization can thereby be obtained against diseases such as kennel cough in dogs and atrophic rhinitis in swine even through the strain of *B. bronchiseptica* is so highly attenuated that it is self-clearing from the respiratory mucosa.

8 Claims, No Drawings

METHOD OF VACCINATION FOR PREVENTION OF *BORDETELLA BRONCHISEPTICA* INFECTION

This is a continuation of application Ser. No. 162,539, filed June 24, 1980, which in turn, is a continuation-in-part of application Ser. No. 967,478, filed Dec. 7, 1978, both abandoned.

BACKGROUND AND PRIOR ART

*Bordetella bronchiseptica* is capable of infecting the respiratory tracts of many animals particularly mammals. *B. bronchiseptica* is the cause of atrophic rhinitis and pneumonia in swine. Harris and Switzer, *Am. J. Vet. Res.*, 30, 1161-1166 (1969). A related disease in swine is commonly referred to as "turbinate atrophy" because following the primary *B. bronchiseptica* infection, the nasal turbinate bones frequently undergo serious deterioration. See Switzer and Farrington U.S. Pat. No. 4,016,253 (1977).

In dogs, *B. bronchiseptica* has been characterized as the primary etiological agent in infectious canine tracheobronchitis more commonly known as kennel cough. Wright et al, *Vet. Rec.*, Nov. 3, 1973, 486-487; Appel et al, Cornell Research Laboratory for Disease of Dogs, Laboratory Report, Series 2, No. 6 (May, 1976). The latter publication states that kennel cough is a highly contagious respiratory disease of dogs which, although not life-threatening, should be prevented. The disease causes suffering to the dogs and is unpleasant for dog owners. It is commonly transmitted when dogs are placed in kennels for boarding.

Other mammalian species are also afflicted with *B. bronchiseptica* infections. These include laboratory animals such as guinea pigs, rabbits, and rats, as well as animals raised for meat or fur, such as rabbits and chinchilla. See Nakagawa et al, *Jap. J. Vet. Sci.*, 33(2), 53-60 (1971); Oldenburg et al, *Monatshefte fur Veterinarmedizin*, 27(19), 738-743 (1972); Burek et al, *Lab. An. Sci.*, 22(6), 844-849 (1972); Ioakimidis et al, *Kteniatrika Nea Thessaloniki*, 2, 31-33 (1970). *B. bronchiseptica* may also cause pneumonia in monkeys and other zoo animals. Graves, *Lab. An. Car.*, 20(2), 246-250 (1970). Cats are carriers of *B. bronchiseptica* and may spread the disease to other animals. Fisk et al, *Lab. An. Sci.*, 23(1) 33-35 (1973).

In the United States, the first successful swine vaccine for preventing turbinate atrophy is manufactured and sold by Burns-Biotec Laboratories, Inc. in accordance with Switzer and Farrington U.S. Pat. No. 4,016,253. This patent describes a parenteral vaccine for intramuscular injection prepared from killed whole cells of strain D-1 (ATCC No. 31124).

In 1973 Daniel O. Farrington and William P. Switzer published positive results of experiments using strain 55 intranasal vaccines for swine. *Proceedings of the George A. Young Conference on Advances in Swine Repopulation and the 13th Annual Nebraska SPF Conference*, Lincoln, Neb., July 23-24, 1973, pp. 44-52. These and related experiments were more completely reported in the Ph.D. thesis of Daniel O. Farrington, entitled "Evaluation of Nasal Culturing Procedures and Immunization as Applied to the Control of *Bordetella bronchiseptica* Rhinitis in Swine." Iowa State University, Ames, Iowa, Dr. William P. Switzer, Major Professor. This thesis is on deposit at the Iowa State University Library, Ames, Iowa under call No. 1974-F 249. This thesis also contains a description of the taxonomic characteristics of strain 55. As described in these Switzer-Farrington publications, a concentrated aqueous suspension of strain 55 cells was prepared by culturing strain 55 in tryptose phosphate broth (TPB), and syringe administering 0.5 ml. of the cell suspension into each nostril of the pig, the cultures used containing approximately $1 \times 10^7$ viable cells per milliliter.

The vaccine developed by Dr. Switzer and Dr. Farrington, as described above, is the subject of U.S. patent application Ser. No. 967,477, filed Dec. 7, 1978, and is administered as an intra-respiratory vaccine. The immunization action is dependent on implant colonization of the respiratory mucosa. Successful implantation relates to the number of viable cells administered, and to the ability of the cells to implant and colonize before they are removed from their respiratory tract. The mucous membranes of the respiratory tract tend to be resistant to the implantation of the cells. On initial administration of the intra-respiratory vaccine containing the viable cells, the ciliated epithelia of the upper respiratory tract respond by trying to clear the cells from the nasal passages. There is also a tendency to clear foreign material from the mouth, throat and tracheae. However, for effective use, a live-cell respiratory vaccine must possess the capability to remain on the respiratory mucosa long enough for the cells to become implanted, form colonies, and thereby create the desired immunizing effect.

Since the cells of strain 55 *B. bronchiseptica* are highly attenuated, being not only avirulent but self-clearing from the respiratory mucosa, the problem of obtaining effective implant colonization presents particular difficulties. For commercial use, it is desirable for economic reasons and for ease of administration to avoid the use of excessive size doses. Moreover, the intra-respiratory administration may be carried out by relatively untrained people, such as swine raisers, dog owners, etc. Yet, immunization must be effectively obtained with each vaccination, and a hit-or-miss immunization is completely unacceptable for general use of the vaccine.

SUMMARY OF INVENTION

This invention is based on the discovery that the use of a critically small amount of a wetting agent in the intrarespiratory vaccine prepared from strain 55 (ATCC No. 31437) cells of *B. bronchiseptica,* or similar avirulent self-clearing strain, enhances the effectiveness of the vaccine. Although wetting agents in general tend to be bactericidal or bacteriastatic, the viability of the cells can be maintained while at the same time promoting the implant colonization of the cells. To accomplish this result, the wetting agent must be selected so that the critically small amount thereof is non-inhibitory to the growth of the cells while being sufficient to promote implantation of the cells in their respiratory mucosa. Very low concentrations of non-ionic or anionic detergents have been found to be particularly suitable. To avoid an adverse effect on the viability of the cells, it is desirable to incorporate the wetting agent in the vaccine immediately prior to administration thereof. For example, the vaccine can be packaged in a two-vial arrangement, one vial containing freeze-dried cells, and the other a sterile dilute aqueous solution of the wetting agent. When it is desired to administer the vaccine, the contents of the two vials can be combined, providing an aqueous suspension of rehydrated viable cells in the presence of the desired low concentration of the wetting agent for promoting the implant colonization. Because of the very low concentration used of the wetting agent, such as the non-ionic surfactant, and because of the relatively short time of contact of the wetting agent with the viable cells, no reduction of viability or inhibition of the growth of the cells is produced, while at the same time the presence of the wetting agent assists the vaccine in spreading on the nasal mucosa, and the successful implantation of the cells to form temporary colonies in the mucosa.

DETAILED DESCRIPTION

The present invention relates to a method of preparing and administering an intra-respiratory vaccine for *Bordetella bronchiseptica* infection, and to a vaccine dose form for use therein. While the infection is preferably practiced with strain 55 (ATCC No. 31437), other attenuated avirulent strains of *B. bronchiseptica* can be used, providing the strain has been adapted for implant colonization of respiratory mucosa, and is self-clearing therefrom. It has been reported in the literature that strain D-1 (ATCC No. 31124) when introduced as a live vaccine into the nasal cavities of non-immune swine will cause a relatively mild infection, and that thereafter the swine are immune to further infection, and are protected against turbinate atrophy. See Switzer and Harris, *J. Vet. Res.*, 30, 1161–1166 (1969). Thus far, however, strain D-1 has not been found to be a practical intranasal vaccine. It has been found that strain D-1 persists in the nasal passages of the swine after recovery from the infection. As distinguished from strain D-1, strain 55 is self-clearing, that is, within a few days or weeks, the colonies of strain 55 in the nasal passages or other respiratory mucosa disappear. For practicing the present invention, the strain employed should have been attenuated to the extent that after colonizing the nasal mucosa it is self-clearing.

When viable cells of strain 55, or comparable strain, are deposited in sufficient numbers in the nasal passages of swine, they multiply and form colonies in the mucous membranes of the nasal passages. The colonies persist for only a few days, and are usually cleared from the nasal passages of swine in less than a week. The same thing happens with dogs except that the colonies persist for a somewhat longer time, several weeks being required for clearance. During the time in which the colonies of strain 55 are present in the nasal passages of the animals, they do not produce any clinical symptoms of disease. However, when used as an intranasal vaccine for non-immune animals subject to *Bordetella bronchiseptica* infection, the resistance of the animals to subsequent infection by virulent *B. bronchiseptica* is significantly increased. The local immunization in the nasal passages inhibits the growth of infectious *B. bronchiseptica*, and greatly accelerates the clearance rate. In swine, clinical symptoms of atrophic rhinitis are prevented, and the secondary effects of turbinate atrophy are greatly reduced. In dogs, clinical symptoms of kennel cough (tracheobronchitis) are prevented.

In one embodiment of the present invention, viable cells of *Bordetella bronchiseptica* strain ATCC No. 31437, which may have been subjected to freeze-drying for preservation, are introduced into a suitable culture medium, which is then incubated at a temperature favoring the growth of the organism. In general, published procedures for culturing *B. bronchiseptica* organisms can be employed. See, for example, *Am. J. Vet. Res.*, 30, 1161, 1162 (1969); and *Am. J. Vet. Res.*, 33, 975, at 1976 (1972). More specifically, tryptose phosphate broth (TPB) may be used for propagation of the organism. One suitable source of such a TPB medium is Difco Laboratories, Inc., Detroit, Mich. Other useable culture mediums include: Bordet:Gengou Agar (Difco), Brain-Heart Infusion Broth (Difco), tryptone soya broth (Oxoid Limited, London, England). Propagation temperatures of 36° to 38° C. are favorable.

The cultured cells are preferably recovered (harvested) without concentration by centrifugation or filtration. Since the cells are to be used live, it is desirable to avoid damage to the cells by mechanical processing. Fortunately, cell cultures having a sufficiently high concentration of the strain 55 cells are obtainable, and the residual fermentation nutrients can remain with the cells for a vaccine administration. In general, the cell culture after fermentation should have a concentration of at least $1 \times 10^7$ viable cells per milliliter. For example, the cell density may range from $1 \times 10^7$ to $1 \times 10^9$ cells/ml.

In practicing the present invention, the cell suspension obtained by fermentation may be subjected to freeze-drying (lyophilization) for preparing the vaccine dose form, which may be stored, shipped, and prepared for administration at the time of the intra-respiratory vaccination. There can be added to the cell suspension prior to freeze-drying, microbiological cryoprotectants and stabilizers, as is known in the art. The cryoprotectant-stabilizer means are added as an aqueous solution, which thereby dilutes the cell concentration. For example, a fermentation cell density of $2 \times 10^8$ cells/ml. may be reduced to $1.3 \times 10^8$ cells/ml. Also, and despite the addition of cryoprotectants, the freeze-drying of the cells will cause a reduction in the content of viable cells. Such loss of viability is inherent in freeze-drying of cells. For example, with strain 55 cells, a cell concentration after addition of the cryoprotectant-stabilizer of $1.3 \times 10^8$ may be reduced during dessication to $2 \times 10^6$. In addition, further loss of cell viability may occur during storage of the freeze-dried cells prior to use. It is therefore difficult to be certain of obtaining sufficiently high concentrations of viable cells in the vaccine as prepared for use.

In accordance with the present invention, after freeze-drying, a measured quantity of the cells is introduced into a vaccine vial for storage and transport. The vial should contain at least one dose of the vaccine, and may contain individual or multiple doses. In general, each vaccine dose should provide at least $1 \times 10^6$ viable cells, such as a dose in the range of $1 \times 10^6$ to $1 \times 10^8$ viable cells.

Prior to administration of the vaccine sterile water is added to the cells in an amount appreciably less than the volume of water removed from the cells by freeze-drying. Preferably, the amount of water added to a quantity of the cells is at least 25% less than the volume of water removed from the cell quantity by the freeze-drying while being sufficient to form an aqueous suspension of the cells for the intra-respiratory administration. For example, the added sterile water may be equal to 40 to 60% of the water removed from the quantity of cells. In this way, the concentration of viable cells may be increased, thereby offsetting the effects of the cell dilution and viability loss.

The sterile water used for reconstituting the cells should contain a wetting agent for promoting the mucosal implantation of the cells. The wetting agent and the amount present should be non-inhibitory with respect to the growth of the cells. Cationic wetting agents are therefore, in general, not suitable because they have marked bacteriostatic action. Non-ionic wetting agents are preferred, but non-inhibitory anionic wetting agents can also be used. For example, the non-ionic wetting agent may be Triton X-100 (octylphenoxypolyethoxyethanol), available from Rohm & Haas Company, Philadelphia, Pa. It has been found that very low concentrations of this wetting agent are effective, such as concentrations in the sterile water of 0.01%. Other non-ionic wetting agents which may be used include Neodol (ethoxylates containing 9–12 carbon atoms), available from Shell Chemical Company, Houston, Tex. Useable anionic wetting agents of very dilute concentrations include sodium lauryl sulfate, tallow alkyl sulfate, and sodium dodecyl sulfate. Other commercially available anionic wetting agents include Orvus AB Granules (linear alkane sulfonates) obtainable from Proctor & Gamble Company, Cincinnati, Ohio, and Conco-AAS-35 (35% sodium dodecyl benzene sulfonate) obtainable from Continental Chemical Co., Clifton, N.J. These wetting agents should be used at very low concentrations for the purpose of the present invention. For other non-ionic or anionic wetting agents that can be used for the purposes of this invention, reference may be made to the Surfactant Science Series: Nonionic (1967); and Anionics (1976); published by Marcel Dekker, Inc., New York, N.Y.

Where the sterile water containing the wetting agent is combined with the freeze-dried cells immediately prior to the administration of the resulting cell suspension, as preferred, the non-inhibitory action of the wetting agent can be observed in terms of the retention of viable cells. In other words, the wetting agent and the amount employed should not be such as to adversely affect the viability of the cells prior to administration. Since the suspension after reconstitution will ordinarily be administered in less than 30 minutes, such as within 10 to 15 minutes after reconstitution, a relatively short term action of the wetting agent is involved. Once the vaccine is administered, the mucosal fluids will further dilute the concentration of the wetting agent, and thereby tend to offset any adverse affect due to wetting agent concentration. However, the concentration of the wetting agent should be kept as low as possible while having sufficient wetting agent present to promote the implantation of the cells in the respiratory mucosa. For example, using Triton X-100 as the wetting agent, concentrations as low as 0.01% can be used, as described above. Where sodium lauryl sulfate is used as a wetting agent, concentrations in the range of 0.01 to 0.1% can be used. It is believed that results are particularly desirable when employing sodium lauryl sulfate at these concentrations.

The mucous membranes of the respiratory tract tend to be resistant to the implantation of the cells. The ciliated epithelia of the upper respiratory tract will respond by trying to clear the cells from the nasal passages. There is also a tendency to clear foreign material from the mouth, throat, and trachae. For effective use, the respiratory vaccine must possess the capability to resist this clearance. The incorporation of the wetting agent in the sterile water used to form the vaccine suspension helps to resist clearance of the cells and to promote their implantation in the mucosa. The wetting agent reduces the surface tension of the mucosal fluids flowing over the respiratory mucosa, thereby achieving a more rapid and closer contact of the viable cells with the mucosal tissue. In this way, the establishment of the cells and their colonization of the mucosal tissue is promoted, and it is this colonization which produces the local immunity to subsequent infection with virulent (pathogenic) *B. bronchiseptica*.

Where the vaccine is applied intranasally, as preferred for swine, it is desirable to introduce the vaccine into each nare. The total vaccine dose (both nares) may range from $1 \times 10^6$ to $1 \times 10^8$, and this amount of cells may be administered in from 0.7 to 1.3 milliliters. For example, a vaccine dose of approximately 0.5 milliliters per nare may be used at a concentration of about $4 \times 10^6$ viable cells per milliliter, thereby $2 \times 10^6$ cells being administered to the mucosa in each nostril.

A similar administration procedure may be used for dogs, that is, intranasal administration. However, it is believed that the easiest and most effective means for using the vaccine with dogs is by intrapharyngeal administration. In clinical kennel cough, the infection is found in the throat of the dog, particularly in the trachea. It has been found that applying a small amount of the cell suspension, such as 0.5 to 1.5 ml. to the upper portion of the pharnyx (nasopharynx) can effectively result in colonization of the mucosa of the pharynx and trachea. The desirable cell densities are the same as for intranasal administration, that is, from about $1 \times 10^6$ to $1 \times 10^8$ cells per milliliter. For example, a concentration of $4 \times 10^6$ is satisfactory. It is believed that the vaccine for both intranasal and intrapharyngeal administration should contain at least $1 \times 10^6$ viable cells per milliliter.

The method of the present invention for preparing and administering intra-respiratory *B. bronchiseptica* vaccines can be practiced conveniently with a 2-vial packaging system. One vial will contain a measured quantity of the freeze-dried cells, and may contain a single or multiple dose quantity. For example, the vial may contain from $1 \times 10^6$ to $1 \times 10^8$ viable cells per dose. A single dose vial, therefore, as an example, might contain $4 \times 10^6$ viable cells. The other vial will contain the sterile water which preferably has the wetting agent dissolved therein, such as 0.01% concentration Triton X-100. The amount of water in the second vial will be substantially less than the water removed by freeze-drying. For example, the second vial may contain 1 ml. of water for reconstitution of the freeze-dried cells in the first vial from which 2 ml. of water were removed in the freeze-drying. More generally, as already indicated, the water in the second vial may equal 40 to 60% of the water removed during the freeze-drying of the cells contained in the first vial. The volume of water to be used should be sufficient to form an aqueous suspension of the cells. Usually, the amount of water will be within the range from 0.7 to 1.3 ml. per cell dose.

The aqueous cell suspension, comprising the vaccine dose, may be administered by a syringe-type applicator, or by spraying the aqueous suspension onto the mucosa. For example, using a standard sterile 1 ml. plastic syringe, 1 ml. of the reconstituted vaccine may be drawn into the syringe, care being taken that the cells have been completely reconstituted and suspended before being filled into the syringe. Using an elongated plastic nasal applicator over the barrel of the syringe, the tip of the applicator may be inserted into the nares for application to the nasal mucosa, or into the mouth for application to the pharyngeal mucosa. For intranasal administration, half of the syringe volume (0.5 ml.) will be introduced into each side of the nose, while the entire contents (1 ml.) will be discharged onto the upper portion of the pharnyx. Alternatively, the aqueous suspension may be applied with an intranasal or intra-oral atomizer, such as the Devilbis Atomizer No. 1633 (Devilbis Company, Somerset, Pa.) or the Canyon Intranasal Atomizer (Sherwood Medical Ind. Inc., St. Louis, Mo.). Using atomizer application, the amounts of the vaccine to be employed can be the same as for syringe application, but, if desired, a larger quantity of the vaccine may be applied.

The cryoprotectants and stabilizers useable for the purpose of the present invention are those well known in the art of bacterial cell preservation. They may also include nutrients. The substances used as cryoprotectants/stabilizers/nutrients for bacterial cells include dextran, gelatin, lactose, sodium glutamate, bovine albumin, digested casein, glutathione, and phosphate salts, such as potassium hydrogen or dihydrogen phosphate. A preferred cryoprotectant-stabilizer additive system will be further illustrated in the following examples, as will other information for practicing the invention.

EXAMPLE I

Strain 55 *B. bronchiseptica* (ATCC No. 31437) was grown into tryptose phosphate broth for 24 hours at 37° C. The culture was agitated by magnetic spin bar, or by the introduction of sterile air during the growth phase. A cell density of $2\times10^8$ cell/ml. was obtained, and was considered acceptable harvest culture. The culture was then formulated with a cryoprotectant-stabilizer system, such as a solubilized casein-lactose formulation, a dextran-sugar combination, glycerol, or a serum-sugar combination. In this experiment, a 3-part formulation was prepared using sterile deionized water as follows:

| | Grams per Liter |
|---|---|
| Solution I | |
| N—Z Amine AS | 150.0 |
| Dextran | 60.0 |
| Gelatin | 4.0 |
| Solution II | |
| Lactose | 200.0 |
| Sodium Glutamate | 4.0 |
| $KH_2PO_4$ | 2.12 |
| $K_2HPO_4$ | 5.0 |
| Bovine Albumin Fraction V | 20.0 |
| Solution III | |
| Glutathione | 50.0 |

The N-Z Amine AS used in Solution I is a pancreatic digest of casein, which forms clear solutions in water. It is obtainable from Sheffield Chemical, Norwich, N.Y. The Bovine Albumin Fraction V used in Solution II is prepared from bovine plasma and forms clear solutions in water. It is obtainable from Miles Research Products, Miles Laboratories, Inc., Elkhart, Ind.

Solution I was sterilized by autoclaving, and Solutions II and III were sterilized by sterile filtration. The solutions were then combined with the strain 55 cell culture in the following proportions:

| | Volume (milliliters) |
|---|---|
| Strain 55 culture ($2\times10^8$ cells/ml.) | 6000 |
| Solution I | 1500 |
| Solution II | 1500 |
| Solution III | 29.7 |

-continued

The vaccine was then filled into sterile vaccine vials at 2 ml. fill volume (1.8 to 2.2 ml. vaccine volume range). The vialed vaccine was then frozen at −50° C., and thereafter dessicated in a commercial freeze-dryer. The viable cell count after drying was approximately $2\times10^6$ cell/milliliter so that each vial contained about $4.0\times10^6$ cells. Cell dilution from addition of the solutions I, II, and III was from about $2\times10^8$ to $1\times10^8$/ml. The loss of viable cells from dessication was from about $1.3\times10^8$ to $2\times10^6$.

A second series of vials is filled with sterile deionized water containing 0.01% Triton X-100, a non-ionic wetting agent (octylphenoxypolyethoxyethanol) obtained from Sigma Chemical Company, St. Louis, Mo. Each vial was filled with 1 ml. of the sterile water containing the non-ionic wetting agent. In preparing the vaccine for intra-respiratory administration to swine or dogs, the contents of the two vials are combined, the 1 ml. of sterile water being added to the individual dose of the freeze-dried cells ($4\times10^6$ cells) providing an aqueous suspension having a volume of approximately 1 ml. with a cell concentration of $4\times10^6$/ml. The reconstituted vaccine dose is then administered intranasally to dogs, 0.5 ml. being introduced into each nostril by syringe or atomizer, or administered intrapharyngeally for dogs, the 1 ml. suspension being introduced into the upper portion of the pharynx by syringe or aerosol.

EXAMPLE II

Strain 55 vaccine was prepared and reconstituted as described in Example I. The reconstituted vaccine was then tested in dogs for properties of respiratory tract colonization after intrapharyngeal route of administration. Fifteen dogs were used in the experiment. The dogs being free of *B. bronchiseptica* and non-immune thereto.

The dogs were divided into two groups of ten and five dogs respectively. The control group (Group I) was maintained in a separate facility while the treated dogs (Group II) were immunized. The freshly reconstituted vaccine was shaken vigorously to be sure that the dried vaccine pellet was fully dissolved and suspended. Each of the ten dogs in Group II were inoculated intrapharyngeally with 1.0 ml. of reconstituted vaccine using a syringe with a nasal applicator. The dogs thereby received approximately $4\times10^6$ viable cells of strain 55. Treated dogs were swabbed twice weekly prior to challenge to demonstrate that 55 strain had properly colonized in the dog's respiratory tract from intrapharyngeal administration. Control dogs in Group I were also swabbed twice weekly to re-verify their negative Bordetella status.

Ten of ten intrapharyngeally inoculated dogs were found to have strain 55 organisms colonizing the respiratory tract at a similar level as found in dogs treated intranasally with 55 strain. Five of five control dogs were maintained negative for the presence of *Bordetella bronchiseptica* organisms.

EXAMPLE III

The effects of different concentrations on the viability of reconstituted cells of strain 55 (ATCC No. 31437)

were reconstituted in sterile water using different concentrations of a non-ionic wetting agent. The wetting agent employed was Triton X-100 (octylphenoxypolyethoxyethanol). Equal quantities of cells were reconstituted with one milliliter of sterile water, without wetting agent, and with concentrations of the wetting agent ranging from 0.001% to 1.0%. The viable cell counts were made within thirty minutes of the reconstitution, simulating the condition which would be used for the reconstitution immediately prior to administration. The data is summarized below in table A. As can be seen, the data indicates that a suitable concentration of the wetting agent for use is 0.01%.

TABLE A

| % Concentration Wetting Agent[1] | Viable Cell Count (CFU's/ml.)[2] |
|---|---|
| None (Control) | $2.7 \times 10^6$ |
| 0.001 | $1.9 \times 10^6$ |
| 0.01 | $2.8 \times 10^6$ |
| 0.1 | $6.5 \times 10^5$ |
| 1.0 | $2.8 \times 10^5$ |

[1] Triton X-100 (octylphenoxypolyethoxyethanol)
[2] Average of two pooled samples

EXAMPLE IV

Strain 55 cells (ATCC No. 31437) are prepared for administration in a two-vial package, described in Example I, except the vial containing the sterile water contains 0.1% sodium lauryl sulfate instead of 0.01% Triton X-100. The cells can be reconstituted and administered without adversely affecting the viability of the cells, while at the same time promoting the mucosal implantation of the cells.

We claim:

1. A method of obtaining effective implant colonization when subjecting an animal subject to *Bordetella bronchiseptica* infection to intra-respiratory vaccination with a live avirulent strain of *B. bronchiseptica* which has been attenuated to the extent that it is self-clearing from the respiratory mucosa of the animal to be immunized, comprising:
   (a) immediately prior to said vaccination combining freeze-dried viable cells of said avirulent self-clearing strain with sterile water containing a wetting agent to form an aqueous suspension of said cells, said suspension containing at least $1 \times 10^6$ of said viable cells per milliliter, the amount of said wetting agent in said suspension being selected to be non-inhibitory to the growth of said cells while promoting implantation of said cells in respiratory mucosa; and
   (b) administering the resulting wetting agent-containing suspension by applying it to the respiratory mucosa of said animal.

2. The method of claim 1 in which said animal is a dog, said immunization is for prevention of kennel cough, and said administration is by intrapharyngeal application.

3. The method of claim 1 in which said animal is a swine, and immunization is for prevention of atrophic rhinitis and turbinate atrophy, and said administration is by intranasal application.

4. The method of claim 1 or claim 2 or claim 3 in which said wetting agent is a non-ionic wetting agent.

5. The method of claim 1 or claim 2 or claim 3 in which said wetting agent is octylphenoxypolyethoxyethanol which is present in said suspension in a concentration of about 0.01% based on the water therein.

6. The method of claim 1 or claim 2 or claim 3 in which said viable cells are cells of the *B. bronchiseptica* strain ATCC No. 31437, and in which said wetting agent is octylphenoxypolyethoxyethanol which is present in said suspension in a concentration of about 0.01% based on the water therein.

7. The method of claim 1 or claim 2 or claim 3 in which said viable cells are cells of the *B. bronchiseptica* strain ATCC No. 31437, and in which said wetting agent is a non-ionic wetting agent.

8. The method of claim 1 or claim 2 or claim 3 in which said viable cells are cells of the *B. bronchiseptica* strain ATCC No. 31437.

* * * * *